US007220725B2

(12) United States Patent
Shulov et al.

(10) Patent No.: US 7,220,725 B2
(45) Date of Patent: May 22, 2007

(54) PHARMACEUTICAL COMPOSITION COMPRISING AN ANALGESIC PEPTIDE AND METHOD FOR TREATING PAIN

(75) Inventors: Aharon Shulov, deceased, late of Jerusalem (IL); by Shlomit Shulov Barkan, legal representative, Mevaseret Zion (IL); Naftali Primor, Jerusalem (IL)

(73) Assignee: S.I.S. Shulov Institute for Science Ltd., Rehovot (IL)

( * ) Notice: Subject to any disclaimer, the term of this patent is extended or adjusted under 35 U.S.C. 154(b) by 449 days.

(21) Appl. No.: 10/344,129

(22) PCT Filed: Aug. 6, 2001

(86) PCT No.: PCT/IL02/00724

§ 371 (c)(1), (2), (4) Date: May 30, 2003

(87) PCT Pub. No.: WO02/12269

PCT Pub. Date: Feb. 14, 2002

(65) Prior Publication Data

US 2004/0014673 A1 Jan. 22, 2004

(30) Foreign Application Priority Data

Aug. 10, 2000 (IL) .................... 137820

(51) Int. Cl.
*A61K 38/00* (2006.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. .................... 514/18; 530/330
(58) Field of Classification Search .............. None
See application file for complete search history.

(56) References Cited

U.S. PATENT DOCUMENTS 4,491,541 A * 1/1985 de Castiglione et al. .... 530/330

| 4,619,916 A | | 10/1986 | Di Stazio et al. |
| 5,776,896 A | * | 7/1998 | Lampe ........................ 514/12 |
| 6,051,683 A | * | 4/2000 | Deigin et al. ............... 530/330 |
| 6,555,109 B1 | * | 4/2003 | Shulov et al. ........... 424/94.67 |
| 2004/0014673 A1 | * | 1/2004 | Shulov et al. ................ 514/18 |

FOREIGN PATENT DOCUMENTS

| DE | 33 40 208 | 5/1984 |
| EP | 0 148 133 | 7/1985 |
| WO | WO 92/19254 | 11/1992 |

OTHER PUBLICATIONS

Kaiser II, F. B., Toxicon 31, pp. 889-899, 1993. (Abstract only).
Huang, Kai-Fa, et al., Characterization of Three Endogenous Peptide Inhibitors for Multiple Metalloproteinases with Fibrinogenolytic Activity from the Venom of Taiwan Habu (*Trimeresurus mucrosquamatus*). Biochem. Biophys. Res. Comm. 248, pp. 562-568, 1998.
Robeva, A., et al., "Synthetic and endogenous inhibitors of snake venom metalloproteinases". Biomed. Biochim. Acta 50, pp. 769-773, 1991.

* cited by examiner

*Primary Examiner*—Anish Gupta
*Assistant Examiner*—Marcela Cordero Garcia
(74) *Attorney, Agent, or Firm*—The Nath Law Group; Gary M. Nath; Susanne M. Hopkins

(57) ABSTRACT

A pharmaceutical composition for topical administration comprising an analgesic effective amount of a peptide comprising L-amino acids of the formula (I): pGLU-X—Y-Z M (I) and a pharmaceutically acceptable excipient. X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null. When Z is any L-amino acid, one but not both of Y and Z is TRP, and when Z is null, Y=TRP. An alkyl group may be attached to an amino acid of the peptide. Also disclosed are the peptide, the preparation of the pharmaceutical composition and a topical method of treating or preventing pain in a mammal.

34 Claims, No Drawings

PHARMACEUTICAL COMPOSITION COMPRISING AN ANALGESIC PEPTIDE AND METHOD FOR TREATING PAIN

FIELD OF THE INVENTION

This invention relates to analgesic peptides and their derivatives.

BACKGROUND OF THE INVENTION

Although pain is a crucially important physiological response, it also results in unnecessary suffering and agony. The control and relief of pain is an important branch of medicine. Pain may come about both as a result of disease as well as a result of medical treatment such as chemotherapy. In either case, it is important to alleviate the pain as much as possible so as to enable the sufferer to function normally.

Two neural pathways relating to pain act concurrently in the body: (1) a sensory pathway which senses tissue damage and subsequently produces a feeling of pain; (2) an analgesic pathway which reduces the feeling of pain and prevents the flow of information about the pain to the central nervous system (CNS), thus allowing the organism to maintain ifs normal activity in spite of an injury. Anesthesia can be realized either by use of a drug which inhibits peripheral nerves that act as pain sensors or by enhancement of the natural analgesic system. Since these are different pathways, they are affected by different substances. For example, aspirin and lidocaine are active on the peripheral sensory pathway, while morphine and related substances are active on the analgesic system.

The most efficient analgesics currently in use are morphine-related substances of opiatic origin. It's well known that the brain makes a variety of endogenous opiates, and this explains the powerful effect of these substances. Their action on neurons is mediated by specialized receptors. Signals regulated by these receptors prevent the flow of information from the peripheral pain neurons to the CNS. These CNS neurons are also sensitive to a variety of other chemical substances including catecholamines (serotonin, noradrenalin etc.), neuroactive peptides (neurotensin) and inhibitory amino acids (glycin and GABA).

U.S. Pat. No. 4,619,916 to Di Stazio discloses 13 new tripeptides of the formula pGLU-X-TRP, where pGLU is cyclized glutamic acid (pyroglutamic acid) and X may be GLY, VAL, GLU, ASP, SER, ALA, ASN, GLN, ILE, LEU, PRO, LYS and ARG. Also disclosed are a process for their preparation, pharmaceutical formulations containing them for oral or parenteral administration and their use as hypotensive and analgesic agents. Further disclosed are lower alkyl esters of the tryptophan residue, in particular methyl or ethyl esters, for use as protecting groups in the production of the peptides. The protecting groups are removed at the completion of the synthesis process. There is no disclosure of a topical formulation.

WO 92/19254 discloses α-substituted mono, di, tri, tetra and pentapeptides useful in treating obesity, anxiety, gastrointestinal ulcers, pain, stroke and inflammation. Peptides of the formula pGLU-X-TRP are not disclosed.

The following tetrapeptides of the formula pGLU-X-TRP-Z appear in the literature:

X=L-Ala; Z=L-LeuOH, L-LeuOCH$_3$, L-LeuNH$_2$, L-MetOH, L-MetOCH$_3$, or L-MetNH$_2$ (DE 3,340,208);

X=Lys; Z=L-AlaOH or L-ProOH (Freer, R. J. and Stewart, J. M. (1971) Cienc. Cult. 23(4):539–42; Francis, B. and Kaiser, I. I. (1993) Toxicon 31(7):889–899);

X=L-Pro; Z=L-ValNH$_2$, L-MetOH, L-MetOCH$_3$, L-MetNH$_2$ L-MetsulfoxideOH, L-MetsulfoxideOCH$_3$, or L-MetsulfoxideNH$_2$ (DE 3,340,208).

SUMMARY OF THE INVENTION

It is an object of the present invention to provide an analgesic pharmaceutical composition which may be administered topically.

It is a further object of the invention to provide novel peptide derivatives.

In a first aspect, the present invention provides a pharmaceutical composition for topical administration comprising an analgesic effective amount of a peptide comprising L-amino acids of the formula (I):

pGLU-X—Y-Z    (I)

wherein X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null, and wherein when Z is any L-amino acid, one but not both of Y and Z is TRP, and when Z is null, Y=TRP, or an analgesic effective amount of a peptide derivative in which an alkyl group is attached to an amino acid of the peptide, and a pharmaceutically acceptable excipient.

It has now been discovered that certain peptides may be used as an active ingredient in topical analgesic compositions.

The active ingredient of the composition of the invention is a peptide of the formula (I). Examples of peptides according to the invention are tripeptides and tetrapeptides in which pGLU is the NH$_2$ terminal amino acid and TRP is at the third (Y) or fourth (Z) amino acid position. Examples of preferred peptides are pGLU-ASN-TRP—OH (pENW), pGLU-GLU-TRP—OH (pEEW), pGLU-ASN-TRP-THR—OH (pENWT), pGLU-ASN-TBR-TRP—OH (pENTW), and pGLU-ASN-TRP-LYS—OH (pENWK).

A peptide derivative according to the invention is one in which an alkyl chain has been attached to the peptide. This can be done by attaching a fatty acid to an amine group, for example to the ε-amine group of a lysine or arginine residue, thus obtaining an alkyl amide of the peptide, or to an hydroxyl group, thus obtaining an alkyl ester of the peptide. The alkyl chain may be attached to any of the amino acids of the peptide capable of reacting with the alkyl chain, as is well known to the skilled man of the art. The alkyl chain may be of any length, but is preferably of medium to long chain length, e.g. 4, 5, 6, 7, 8, 9, 10, 11, 12, 13, 14, 15, 16, 17, 18, 19, 20, 21, 22, 23, 24, 25, 26, 27, 28, 29 or 30 carbons. Examples of peptide derivatives are pGLU-ASN-TRP-LYS(octanoyl)-OH (pENWK—C8) and pGlu-Asn-Trp-O-octyl (pENW—C8).

An "analgesic effective amount" is an amount of active ingredient capable of bringing about the desired pharmacological effect, i.e. the reduction or prevention of pain. This amount depends on a number of parameters such as the exact composition of the active ingredient and carrier, the location of administration, the source of the pain, etc. The amount can be easily determined by the average skilled man of the art by carrying out a limited amount of dose response experiments, e.g. by applying a range of concentrations of a given formulation to a specified location on the body.

Examples of concentrations that have been found to be effective include, but are not limited to, 0.0015–0.02 mg/g carrier.

The pharmaceutical composition of the invention is formulated for topical administration. Such a composition would also comprise one or more pharmaceutically acceptable carriers or excipients such as a mixture of Lanolin and Vaseline for topical use in an ointment, cream or salve. Other carriers for topical use are well known to the skilled man of the art and are included in the scope of the invention. Fragrance-emitting, stabilizers, colorants, thickening agents and other conventional substances may be included in the composition.

The invention also provides a use of an analgesic effective amount of a peptide comprising L-amino acids of the formula (I):

pGLU-X—Y-Z                                                                (I)

wherein X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null, and wherein when Z is any L-amino acid, one but not both of Y and Z is TRP, and when Z is null, Y=TRP, or of an analgesic effective amount of a peptide derivative in which an alkyl group is attached to an amino acid of the peptide, in the preparation of a topical pharmaceutical composition for the treatment or prevention of pain.

A further aspect of the invention is a method of treating or preventing pain in a mammal comprising topically administrating to the mammal an analgesic effective amount of a peptide comprising L-amino acids of the formula (I):

pGLU-X—Y-Z                                                                (I)

wherein X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null, and wherein when Z is any L-amino acid, one but not both of Y and Z is TRP, and when Z is null, Y=TRP, or an analgesic effective amount of a peptide derivative in which an alkyl group is attached to an amino acid of the peptide.

The topical administration of the peptide may be in a conventional manner for topical compositions.

As the composition of the invention sometimes acts after a lag period, it is to be expected that it will be especially effective with respect to chronic pain, although it may be used to treat any type of pain.

In a still further aspect, there is provided a peptide comprising L-amino acids of the formula (I):

pGLU-X—Y-Z                                                                (I)

wherein X is an amino acid selected from the group consisting of GLY, VAL, GLU, ASP, SER, ALA, ASN, GLN, ILE, LEU, PRO, LYS and ARG, Y is TRP or THR, and Z is any L-amino acid, or Z is null, and wherein when Z is any L-amino acid, one but not both of Y and Z is TRP, and when Z is null, Y=TRP, or a derivative of the peptide in which an alkyl group is attached to an amino acid, wherein the length of the alkyl is C4 or longer, with the proviso that when Z is any L-amino acid, if X=ALA, Z is not LEU or MET, if X=LYS, Z is not ALA or PRO, and if X=PRO, Z is not VAL or MET, and with the further proviso that when Z is null, the peptide has the alkyl group attached to an amino acid thereof.

These peptides are unknown in the literature.

A further embodiment of this aspect of the invention is a pharmaceutical composition for treatment or prevention of pain comprising an analgesic effective amount of the peptide of the invention or of an alkyl ester or amide thereof. The pharmaceutical composition may be administered orally, parenterally or topically.

DETAILED DESCRIPTION OF EMBODIMENTS

Methods and Materials

Preparation of Peptide and Derivatives

1. Synthesis of pGlu-Asn-Trp-Lys(Octanoyl)-OH

In one embodiment of the invention, the synthesis of the peptide was carried out manually by a stepwise 9-fluorenylmethoxycarbonyl (Fmoc) solid phase peptide synthesis (SPPS) procedure on Fmoc-Lys(Mtt)-Wang resin (loading of 0.25 mmole on 1 g of preloaded resin).

At the first step the Mtt (4-methyltrityl) protecting group was selectively removed by treatment with 1% TFA in DCM. Octanoic acid was attached to the free amino group (via an amide bond) by regular coupling procedure applying 2-(1H-Benzotriazole-1-yl)-1,1,3,3-tetramethyluronium hexafluorophosphate (HBTU) reagent in the presence of N-hydroxybenzotriazole (HOBt). The same coupling method was applied for the attachment of other amino acids as well. Completion of the coupling step was detected by the Kaiser test (a few resin beads from the reaction are washed with ethanol and transferred into a small glass tube; 2 drops of the following solutions are added: ninhydrin 5% in ethanol, phenol 80% in ethanol, potassium cyanide 0.00002M in pyridine; the sample is mixed and heated to 120° C. for 4–6 minutes. A positive test is indicated by blue resin beads). The Fmoc group was then removed by 20% piperidine, and after washing of the resin the second amino acid (Fmoc-Trp(Boc)) was introduced to restart another coupling step.

These steps were repeated each time with an additional amino acid according to the peptide sequence. The amino acids used were Fmoc-N$^{\alpha}$ protected. Trifunctional amino acids were side-chain protected as follows: Trp(Boc), Asn (Trt). Each Fmoc amino was activated in situ using HBTU/HOBt and subsequently coupled to the resin for 50 minutes. Diisopropylethylamine (DIEA) was used during coupling as an organic base. The Fmoc protecting group on the α-amine was then removed with 20% piperidine in N-methylpyrrolidone (NMP) for 20 min. Three equivalents of the activated amino acids were employed in the coupling reactions. The deprotection and coupling steps were repeated with the addition of each subsequent amino acid until the peptide synthesis was completed. The peptide-resin was washed with NMP, followed by DCM, and dried under vacuum.

This peptide, prepared as described above, was cleaved from the resin using a 95% TFA, 5% triisopropylsilane (TIS) solution for 2 hours at room temperature. The product was precipitated by the addition of 10 volumes of ether, filtered and dried in vacuum. Typically, 150 mg of the peptide was obtained from 1 g of peptide-resin. It was identified by LC/MS ($M^{+1}$=684.7).

Purification

The crude peptide was purified on a preparative RP-HPLC column ($C_{18}$ 5 μm Phenomenex Luna column, 10 mm I.D.×25 cm). The chromatography was done under the following conditions: A=$H_2O$/TFA 0.05%; B=ACN/TFA 0.05%; λ=214 nm; flow=5 ml/min. 50 mg peptide were loaded on the column. A gradient of 15% to 50% B at 45 min was used. Fractions of the main peak were collected and characterized by analytical HPLC. Best fractions were combined together and lyophilized to obtain the required product, which was >95% pure.

2. Preparation of pGlu-Asn-Trp-O-octyl

Preparation of this peptide may also be carried out via a solution synthesis protocol containing following steps:

a. Preparation of Boc-Trp-O-octyl (octyl ester of Boc-Trp)

Boc-Trp (6.1 mmole), octanol (6.8 mmole), DMAP (0.74 g, 6.1 mmole), and dicyclohexylcarbodiimide (DCC) (1.4 g, (6.8 mmole) are introduced to DCM (40 ml) at 0° C. The mixture is stirred and the cooling bath is removed so that the temperature slowly rises to room temperature. The reaction is stirred overnight and then is filtered to remove the dicyclohexylurea (DCU). The solid is washed with DCM and the combined mother liqueur is adjusted to pH=4–5 HCl (0.1 N). The organic phase is washed by water (3×30 ml), dried over $MgSO_4$, filtered and evaporated to obtain crude product.

b. Removal of Boc Group

Boc-Trp-O-octyl is dissolved in ether at room temperature. HCl (4N) in dioxane is introduced (4:1 molar excess) and the reaction mixture is stirred for ca 1 h. Unprotected product precipitates as the HCl salt. It is filtered, washed with ether and dried.

c. DCC/HOBt Coupling Procedure

Boc protected amino acid (14.2 mmole) in DCM (35 ml) is cooled to 0° C. HOBt.$H_2O$ (12.9 mmole, 1.75 g) and DCC (15.5 mmole, 3.2g) are added to a reaction mixture and vigorously stirred for 1 h. Deprotected peptide (after removal of the Boc group) dissolved in DCM (20 ml) and TEA (18.1 mmole) is introduced and the mixture is stirred for an additional 30 min. at 0° C. The cooling bath is removed and the reaction is left overnight at room temperature.

Products mixture is evaporated to dryness under reduced pressure and EtOAc (150 ml) is added. Insoluble particles (DCU) are removed by filtration and mother liquor is washed with brine (2×35 ml), $NaHCO_3$ (5%; 2×35 ml), and water 2×35 ml). The organic phase is dried over $MgSO_4$, and evaporated under reduced pressure.

At the end of the peptide synthesis (the last stage being the coupling of pGlu) a peptide is obtained as a crude product. It is identified by LC/MS and purified similarly to the first peptide (pGlu-Asu-Trp-Lys(octanoyl)-OH).

3. Purification from Snake Venom

Some of the peptides of the invention may also be isolated from snake venom, including venom obtained from snakes of the Viperidae, Elapidae and Crotalidae families. For example, pENW may be purified from *Naja melanoleuca* venom on a Mono Q column using 20 mM Tris-HCl buffer, pH 7.0. The fraction which elutes from the Mono Q column at 12–18 minutes (with a peak at 14.3 minutes) is further purified on HPLC as follows. The fraction is loaded onto an HPLC Spherisorb 5 column, 5μ, 250×4.6 mm, phase Sep. S/N 142110, and eluted using a gradient of 20 mM $NH_4Ac$ (pH 5.5) and AcN. In an alternate purification, the venom may be purified on the Mono Q column using 20 mM ammonium acetate buffer, pH 6.9. The fraction with a peak at 17 minutes is further purified by HPLC as described above. NMR, HPLC and LC/MS analyses revealed the identity of the synthetic and natural peptides.

Similarly, pENW, pEEW and pENTW or pENWT have been purified from *Crotalus adamanteus* venom, and pENW has been purified from *V. palestinae* venom.

Assays

1. Analgesic Assay

In each test, a few tens of hamsters of similar weight and age were used. The hamsters were divided into groups according to the number of samples to be tested. Ointment (50% Lanolin and 50% Vaseline) containing the tested substance was applied to the animal's fur on the back region. The fur was not removed so as to ensure that no damage to the skin occurred. A control group of hamsters was treated with ointment without the fraction of the invention. Hamsters were treated by topical application for 6, 14, 21 or 28 consecutive days. The test for analgesity was conducted following the last application of the ointment. In an alternate protocol, analgesity was tested following a single application of the ointment.

Subsequently to application of the ointment, the hamsters "clean" themselves by dispersing the ointment all over their body with their tongue and legs. Thus, some of the ointment is introduced into the oral cavity and possibly also into the intestine of the hamsters.

In a typical test, a constant amount of ointment with or without an analgesic substance is applied to each animal for a predetermined period of one or more days. Following this period, pain is induced by a subcutaneous injection of 0.5 ml of 1N HCl/0.1 kg body weight in the femur region. The hamsters respond to the HCl injection by touching the area of injection with the tongue, this being called a "lick". 20 minutes after injection the hamster is observed for 60 min and the number of "licks" are counted. The number of "licks" serves as a quantitative indication of the HCl induced pain.

The analgesic effect is determined by comparing the mean number of "licks" in control animals to the number in treated animals. The significance of the difference was determined using t-test statistics.

EXAMPLE 1

0.6 mg of pENW, pENWK-C8 or pENWGAT (a dimer of pENW) were dissolved in 5 ml of DDW, mixed by an ultrasonic mixer for 2 minutes and then dissolved in 315 gr of ointment. The final peptide concentration was 0.002 mg/gr.

6 applications were made over a period of 4 weeks. The test for analgesity was conducted 10 days following the last application of the ointment. The results are summarized in the following table:

| active ingredient | number of animals | mean number of licks | Std. Dev. | SEM | p* |
|---|---|---|---|---|---|
| control | 25 | 113.9 | 69.1 | 13.8 | — |
| pENW | 27 | 59.7 | 58.9 | 11.3 | 0.0017 |
| pENWK-C8 | 28 | 37.9 | 34.8 | 6.6 | <0.0001 |
| pENWGAT | 32 | 117.0 | 81.2 | 14.4 | 0.9872 |

*Mann-Whitney rank sum test

It can be clearly seen that the topical application of the tripeptide had a significant effect on reducing the pain of the animals, and that the tetrapeptide derivative was even more effective. The addition of 3 amino acids to the C-terminal of the tripeptide completely abolished its activity.

EXAMPLE 2

Compositions at a concentration of 0.020 mg/g were prepared as in Example 1 containing the following active ingredients: pENW, pEEW, or pENTW or pENWT. 6 applications were made over a period of 5 weeks. The results are summarized below:

| active ingredient | number of animals | mean number of licks | SEM | p* |
|---|---|---|---|---|
| control | 24 | 117 | 6 | — |
| pENW | 25 | 44 | 31 | <0.05 |
| pEEW | 26 | 35 | 30 | <0.05 |
| pENTW or pENWT | 25 | 39 | 26 | <0.05 |

*Dunn's method

It can be seen that all of the assayed peptides have significant analgesic activity.

EXAMPLE 3

A composition containing pENW—C8 at a concentration of 0.002 mg/g ointment was prepared as in Example 1. A single application was made to the animals, and analgesity was assayed 11, 23 and 48 days post-application. Ointment without an active substance was applied to the control animals.

The results summarized below:

| # of days post application | number of animals | mean number of licks | SEM | p* |
|---|---|---|---|---|
| control | 26 | 106 | 11.2 | — |
| 11 | 28 | 66 | 10 | <0.05 |
| 23 | 27 | 35.7 | 6.5 | <0.05 |
| 48 | 21 | 62.4 | 11 | <0.05 |

*Dunn's method

The results indicate that the analgesic effect builds over time, reaching a peak after around 23 days, and subsequently declines.

The invention claimed is:

1. A topical pharmaceutical composition, consisting of a pharmaceutically acceptable excipient, and an analgesic effective amount of
a peptide comprising L-amino acids of the formula

pGlu-X—Y-Z     (I), wherein
X is an amino acid selected from the group consisting of GLY, VAL, GLU, ASP, SER, ALA, ASN, GLN, ILE, LEU, PRO, LYS and ARG,
Y is TRP or THR, and
Z is any L-amino acid, or Z is null; wherein Z is any L-amino acid, one but not both of Y and Z is TRP, and when Z is null, Y=TRP, or
a peptide thereof having a ($C_2$–$C_{30}$) alkyl group attached thereto, wherein the topical pharmaceutical composition is formulated for topical administration.

2. The pharmaceutical composition according to claim 1, wherein said alkyl group is attached by an amide linkage.

3. The pharmaceutical composition according to claim 1, wherein said alkyl group is attached by an ester linkage.

4. The pharmaceutical composition according to claim 1, wherein X is ASN.

5. The pharmaceutical composition according to claim 1, wherein said alkyl is selected from the group consisting of $C_4$–$C_{30}$.

6. The pharmaceutical composition according to claim 5, wherein said alkyl is an octyl group ($C_8$).

7. The pharmaceutical composition according to claim 1, wherein said peptide is a tetrapeptide.

8. The pharmaceutical composition according to claim 1, wherein said peptide is a tripeptide and Z is null.

9. A method of treating pain, comprising topically administering to a subject in need thereof an analgesic effective amount of
a peptide consisting of L-amino acids of the formula

pGlu-X—Y-Z     (I)

wherein
X is an amino acid selected from the group consisting of GLY, VAL, GLU, ASP, SER, ALA, ASN, GLN, ILE, LEU, PRO, LYS and ARG,
Y is TRP or THR, and
Z is any L-amino acid, or Z is null; wherein Z is any L-amino acid, one but not both of Y and Z is TRP, and when Z is null,
Y=TRP; or
a peptide thereof having an alkyl group attached thereto.

10. The method according to claim 9, wherein said alkyl group is attached by an amide linkage.

11. The method according to claim 9, wherein said alkyl group is attached by an ester linkage.

12. The method according to claim 9, wherein X is ASN.

13. The method according to claim 9, wherein said alkyl is selected from the group consisting of $C_4$–$C_{30}$.

14. The method according to claim 13, wherein said alkyl is an octyl group ($C_8$).

15. The method according to claim 9, wherein said peptide is a tetrapeptide.

16. The method according to claim 9, wherein said peptide is a tripeptide and Z is null.

17. A method of treating pain, comprising topically administering to a mammal an analgesic effective amount of
a peptide consisting of L-amino acids of chemical formula

pGlu-X—Y-Z     (I)

wherein
X is an amino acid selected from the group consisting of GLY, VAL, GLU, ASP, SER, ALA, ASN, GLN, ILE, LEU, PRO, LYS and ARG,
Y is TRP or THR, and
Z is any L-amino acid, or Z is null; wherein Z is any L-amino acid,
one but not both of Y and Z is TRP, and when Z is null, Y=TRP; or
a peptide thereof having an alkyl group attached thereto.

18. The method according to claim 17, wherein said alkyl group is attached by an amide linkage.

19. The method according to claim 17, wherein said alkyl group is attached by an ester linkage.

20. The method according to claim 17, wherein X is ASN.

21. The method according to claim 17, wherein said alkyl is selected from the group consisting of $C_4$–$C_{30}$.

22. The method according to claim 21, wherein said alkyl is an octyl group ($C_8$).

23. The method according to claim 17, wherein said peptide is a tetrapeptide.

24. The method according to claim 17, wherein said peptide is a tripeptide and Z is null.

25. A peptide comprising L-amino acids of chemical formula

pGlu-X—Y-Z        (I)

wherein
X is an amino acid selected from the group consisting of GLY, VAL, GLU, ASP, SER, ALA, ASN, GLN, ILE, LEU, PRO, LYS and ARG,
Y is TRP or THR, and
Z is any L-amino acid; wherein one but not both of Y and Z is TRP; or
a peptide thereof having a ($C_5$–$C_{30}$) alkyl group attached thereto, wherein X and Y are as defined hereinabove, and Z is any L-amino acid, or Z is null; wherein when Z is any L-amino acid, if X=ALA, Z is neither LEU nor MET, if X=LYS, Z is neither ALA nor PRO, and if X=PRO, Z is neither VAL nor MET.

26. The peptide according to claim 25, wherein said alkyl is selected from the group consisting of $C_5$–$C_{30}$.

27. The alkyl ester according to claim 26, wherein said alkyl is an octyl group ($C_8$).

28. A tetrapeptide according to claim 25.

29. A tripeptide according to claim 25.

30. A pharmaceutical composition for treatment of pain, comprising an analgesic effective amount of the peptide according to claim 25.

31. A pharmaceutical composition for treatment or prevention of pain, comprising an analgesic effective amount of the alkyl ester or alkyl amide of a peptide according to claim 25.

32. The method according to claim 9, wherein said peptide is pGlu-Asn-Trp-Thr, pGlu-Asn-Thr-Trp, or pGlu-Asn-Trp-Lys-$C_8$.

33. The pharmaceutical composition according to claim 1, wherein said peptide is pGlu-Asn-Trp-Thr, pGlu-Asn-Thr-Trp, or pGlu-Asn-Trp-Lys-$C_8$.

34. The pharmaceutical composition according to claim 25, wherein said peptide is pGlu-Asn-Trp-Thr, pGlu-Asn-Thr-Trp, or pGlu-Asn-Trp-Lys-$C_8$.

* * * * *